United States Patent
Frantzen

[19]

[11] Patent Number: 6,086,455
[45] Date of Patent: Jul. 11, 2000

[54] APPARATUS FOR POLISHING SURGICAL STENTS

[75] Inventor: John J. Frantzen, Copperopolis, Calif.

[73] Assignee: Cook Incorporated, Bloomington, Ind.

[21] Appl. No.: 09/021,763

[22] Filed: Feb. 11, 1998

Related U.S. Application Data

[62] Division of application No. 08/870,962, Jun. 6, 1997, Pat. No. 5,746,691.

[51] Int. Cl.⁷ .................................. B24B 7/00; B24B 9/00
[52] U.S. Cl. ......................... 451/36; 451/113; 451/114; 451/365; 451/446; 451/381
[58] Field of Search ............................. 451/36, 104, 113, 451/114–118, 165, 365, 389, 446, 910, 381–382, 600, 623, 606

[56] References Cited

U.S. PATENT DOCUMENTS

| | | |
|---|---|---|
| 3,521,412 | 7/1970 | Mccarty ........................... 451/36 |
| 3,698,408 | 10/1972 | Jacke ............................. 451/910 |
| 3,728,821 | 4/1973 | Perry ............................... 451/36 |
| 4,302,418 | 11/1981 | Cullis et al. . |
| 4,704,126 | 11/1987 | Baswell et al. . |
| 4,724,853 | 2/1988 | Hirose . |
| 4,858,264 | 8/1989 | Reinhart . |
| 4,936,057 | 6/1990 | Rhoades . |
| 5,054,247 | 10/1991 | Rhoades et al. . |
| 5,108,417 | 4/1992 | Sawyer . |
| 5,133,732 | 7/1992 | Wiktor . |
| 5,139,480 | 8/1992 | Hickle et al. . |
| 5,195,984 | 3/1993 | Schatz . |
| 5,199,226 | 4/1993 | Rose . |
| 5,242,399 | 9/1993 | Lau et al. . |
| 5,314,444 | 5/1994 | Gianturco . |
| 5,421,955 | 6/1995 | Lau et al. . |
| 5,425,739 | 6/1995 | Jessen . |
| 5,441,515 | 8/1995 | Khosravi et al. . |
| 5,443,477 | 8/1995 | Marin et al. . |
| 5,494,029 | 2/1996 | Lane et al. . |
| 5,496,277 | 3/1996 | Termin et al. . |
| 5,507,767 | 4/1996 | Maeda et al. . |
| 5,507,771 | 4/1996 | Gianturco . |

(List continued on next page.)

FOREIGN PATENT DOCUMENTS

| | | |
|---|---|---|
| 95302708 | 4/1994 | European Pat. Off. . |
| 0712614 | 5/1996 | European Pat. Off. . |
| 0734699 | 10/1996 | European Pat. Off. . |

Primary Examiner—Eileen P. Morgan
Attorney, Agent, or Firm—Richard J. Godlewski; Anton P. Ness

[57] ABSTRACT

A method for polishing radially expandable surgical stents is disclosed where fluid abrasive media M flows over surfaces of the stent 10 causing the surfaces of the stent 10 to be polished and streamlined. The stent 10 is temporarily provided with cylindrical support ends 20, which are not radially expandable to support the stent 10 during the polishing process. An interior polishing fixture 100 is provided which has cylindrical chambers 135 therein adapted to receive a stent 10 therein. Fluid abrasive media M then flows into bores 108 in the fixture 100 leading to the cylindrical chambers 135 and adjacent the inner diameter surfaces of the stent 10. Surfaces of the stent 10 forming the outer diameter are polished by placing the stent 10 within an exterior polishing fixture 200 which has a cylindrical recess 220 therein. The cylindrical recess 220 has a diameter greater than a diameter of outer surfaces of the stent 10 and includes a cylindrical shaft 270 passing axially through the cylindrical recess 220 upon which the stent 10 is located. Slanted bores 208 pass through walls of the exterior polishing fixture 200 and into the cylindrical recess 220, directing the abrasive media M adjacent exterior surfaces of the stent 10 and causing polishing of the exterior surfaces of the stent 10. The direction of abrasive media M flow can be reversed to make streamlining of segments of the stent 10 occur in a symmetrical fashion. After polishing of the stent 10 is completed, the cylindrical support ends 20 are removed and the stent 10 is ready for implantation and radial expansion within a body lumen L. When polished and streamlined, the radially expandable surgical stent 10 more effectively supports a body lumen L without excessive thrombus, restenosis and other medical complications.

12 Claims, 7 Drawing Sheets

U.S. PATENT DOCUMENTS

| | | |
|---|---|---|
| 5,514,154 | 5/1996 | Lau et al. . |
| 5,522,882 | 6/1996 | Gaterud et al. . |
| 5,531,741 | 7/1996 | Barbacci . |
| 5,549,662 | 8/1996 | Fordenbacher . |
| 5,603,721 | 2/1997 | Lau et al. . |
| 5,718,713 | 2/1998 | Frantzen . |
| 5,746,646 | 5/1998 | Shibano ................................ 451/165 |
| 5,746,691 | 5/1998 | Frantzen . |
| 5,788,558 | 8/1998 | Klein . |

APPARATUS FOR POLISHING SURGICAL STENTS

CROSS-REFERENCE TO RELATED APPLICATIONS

This application is a divisional of U.S. patent application Ser. No. 08/870,962 filed Jun. 6, 1997, now U.S. Pat. No. 5,746,691.

FIELD OF THE INVENTION

The following invention relates to the polishing of radially expandable surgical stents which can be surgically implanted into a body lumen, such as an artery, and be radially expanded to support the lumen. More specifically, this invention relates to fixtures used for supporting a radially expandable surgical stent while an abrasive media is flowed over surfaces of the stent to polish the stent and provide an inner surface of the stent with a streamlined contour, and methods for using such fixtures while polishing surgical stents.

BACKGROUND OF THE INVENTION

Surgical stents have long been known which can be surgically implanted into a body lumen, such as an artery, to reinforce, support, repair or otherwise enhance the performance of the lumen. For instance, in cardiovascular surgery it is often desirable to place a stent in the coronary artery at a location where the artery is damaged or is susceptible to collapse. The stent, once in place, reinforces that portion of the artery allowing normal blood flow to occur through the artery. One form of stent which is particularly desirable for implantation in arteries and other body lumens is a tubular stent which is formed as a complete tubular cylinder and can be radially expanded from a first smaller diameter to a second larger diameter. Such radially expandable stents can be inserted into the artery by being located on a catheter and fed internally through the arterial pathways of the patient until the unexpanded stent is located where desired. The catheter is fitted with a balloon or other expansion mechanism which exerts a radial pressure outward on the stent, causing the stent to expand radially to a larger diameter. Such expandable stents exhibit sufficient rigidity after being expanded that they will remain expanded after the catheter has been removed.

Radially expandable stents come in a variety of different configurations to provide optimal performance in various different particular circumstances. For instance, the patents to Lau (Pat. Nos. 5,514,154, 5,421,955, and 5,242,399), Baracci (Pat. No. 5,531,741), Gaterud (Pat. No. 5,522,882), Gianturco (Pat. Nos. 5,507,771 and 5,314,444), Termin (Pat. No. 5,496,277), Lane (Pat. No. 5,494,029), Maeda (Pat. No. 5,507,767), Marin (Pat. No. 5,443,477), Khosravi (Pat. No. 5,441,515), Jessen (Pat. No. 5,425,739), Hickle (Pat. No. 5,139,480), Schatz (Pat. No. 5,195,984), Fordenbacher (Pat. No. 5,549,662) and Wiktor (Pat. No. 5,133,732), each include some form of radially expandable stent for implantation into a body lumen.

Some problems which have been exhibited by prior art stents include that the inner and outer surfaces of the stents are not sufficiently streamlined or finely enough polished to prevent certain medical complications. For instance, thrombus, a phenomenon where a fibrous clot forms within cracks and other irregularities in the surface finish of an implanted object (such as a stent), is enhanced when the surfaces of the stent are not finely polished. Additionally, when the inner surface of the stent is substantially planar and has abrupt edges along borders thereof, turbulence is introduced into the blood. When a stent having such an abrupt edge is implanted into an artery, plaque and other deposits are provided with a site for collection and potential narrowing of the arteries and restriction of blood flow. This plaque buildup adjacent an implanted object (such as a stent) is referred to as "restenosis."

While many prior art stents do exhibit somewhat polished surfaces, they are typically not sufficiently finely polished, especially on tubular stents having smaller diameters, to prevent restenosis and thrombus adjacent the stent after the stent is implanted into the artery. Such prior art stents also lack a streamlined contour to minimize disruption of bodily fluid flow through the lumen and to further discourage restenosis surrounding the stent.

A primary reason why prior art stents fail to exhibit sufficiently finely polished surfaces to avoid the drawbacks discussed above is the lack of a polishing process which can effectively provide the finely polished surface desired, especially on stents having smaller inner diameters. Stents are typically polished in one of two processes, either chemical etching or electropolishing. With chemical etching, chemicals are used which react chemically with the material forming the stent, causing the material forming the stent to be driven into solution. Chemicals are selected which have a strength sufficient to cause rough areas of the stent to be dissolved, but not so strong that smooth areas of the stent are detrimentally altered. Chemical etching, while somewhat effective in removing gross irregularities from the surfaces of the stent, fail to adequately provide the desired finely polished surface.

Electropolishing typically involves providing an electrolytic solution, placing the stent within the electrolytic solution, placing a cathode within the solution and not contacting the stent and coupling an anode to the stent. When an electric voltage is provided between the anode and the cathode, the stent is caused to lose portions of its outer surface when the elements forming the stent are driven into solution and carried to the cathode for deposition upon the cathode. In essence, such electrolytic polishing is the reverse of commonly used electrical plating processes with material from the surface of the stent being removed rather than added to the stent. The rougher surfaces of the stent are more readily driven into solution and hence removed from the surfaces of the stent, smoothing the surfaces of the stent somewhat.

Because the surfaces of the stent forming the inner diameter of the stent benefit from a high degree of polishing, one known technique is to form the cathode as a thin wire passing along a central axis of the stent entirely through the stent from one end to the other, but without physically contacting the stent. When a voltage is provided between the cathode wire passing along the central axis of the stent and the stent itself, the inner surfaces of the stent are provided with the greatest electric field density and hence are the surfaces which are most polished during this process. While typically more effective than chemical etching, electrolytic polishing also fails to provide a sufficiently finely polished stent to significantly discourage thrombus and restenosis adjacent surfaces of the stent.

Accordingly, a need exists for a method and apparatus for polishing surfaces of a radially expandable surgical stent, and particularly the surfaces forming the inner diameter of the stent, with a sufficient degree of polish to reduce or eliminate the occurrence of thrombus and restenosis when surgical stents are implanted within a body lumen.

SUMMARY OF THE INVENTION

The radially expandable surgical stent which is polished and streamlined by the method and apparatus of this invention exhibits an overall tubular cylindrical hollow seamless contour which can feature any of a variety of different arrangements for individual elements and segments forming the stent. The various different segments of the stent have a generally elongate, substantially constant cross-sectional contour which can either be oriented to extend axially, circumferentially, or some combination thereof, with each segment located between an inner diameter of the stent and an outer diameter of the stent. Each segment includes an outer surface coextensive with the outer diameter of the stent and an inner surface coextensive with the inner diameter of the stent. Each segment also includes lateral surfaces extending between the inner surface and the outer surface which can either be a leading surface on an upstream side of the segment, a trailing surface on a downstream side of the segment, or a lateral surface generally aligned axially with the stent.

The inner surface of each segment of the stent is extensively streamlined by the polishing method and apparatus of this invention to minimize disruption of bodily fluid flow through the body lumen. Specifically, the inner surface includes an inner leading edge and an inner trailing edge bordering the inner surface. Each inner edge is defined by an inner curve having a relatively large radius of curvature when compared to the radii of curvature exhibited by outer edges adjacent the outer surface of each stent segment. Because the inner edges have a large radius of curvature, they do not present any abrupt transition in flow for bodily fluids passing over the inner surface of the stent segment, particularly when the stent segment is aligned circumferentially with bodily fluid flow passing adjacent the inner surface from a leading inner edge to a trailing inner edge.

The surfaces of each stent segment are honed and polished to have a surface finish which is free from abrupt transitions and irregularities, such as prominences extending more than five micro inches above adjacent portions of the surrounding surface. Smooth flow of blood or other bodily fluids over the surfaces of the stent can thus be preserved and a risk of medical complications such as restenosis and thrombus can be minimized.

The polishing apparatus of this invention includes a fixture which rigidly supports at least one radially expandable surgical stent within a cylindrical chamber in the fixture. A bore passes through the fixture and leads both into the cylindrical chamber and out of the cylindrical chamber. A source of fluid abrasive media is placed adjacent the fixture in an orientation which allows the fluid abrasive media to pass through the bores and into the cylindrical chamber. The cylindrical chamber has a diameter similar to the outer diameter of the stent so that the fluid abrasive media is forced to pass only through the interior of the stent and adjacent the surfaces forming the inner diameter of the stent. As the fluid abrasive media passes through the cylindrical chamber and adjacent the surfaces forming the inner diameter of the stent, the surfaces forming the inner diameter of the stent are polished to a level of smoothness determined by the particle size of the abrasive media, the amount of time which the abrasive media flows past the surfaces of the stent and other factors known in the honing arts.

When it is desired that the outer diameter of the stent be polished, a stent exterior polishing fixture is provided having a cylindrical recess located therein with slanted bores leading from a top and bottom of the fixture to the cylindrical recess. The cylindrical recess has a diameter greater than the diameter of the outer diameter of the stent. A shaft is located within the cylindrical recess with a central axis of the shaft aligned with a central axis of the cylindrical recess. The shaft has a diameter similar to the inner diameter of the stent. The stent is placed on the shaft and within the cylindrical recess so that abrasive media flowing through the slanted bores and into the cylindrical recess are precluded from flowing adjacent the surfaces forming the inner diameter of the stent, but rather flow adjacent surfaces forming the outer diameter of the stent for polishing of the outer diameter of the stent.

In utilizing the various fixtures for supporting the stent during this polishing process, the stent is preferably initially provided with non-radially expanding cylindrical support ends adjacent each end of the stent. These cylindrical support ends are located along with the stent within the cylindrical chamber or cylindrical recess of one of the fixtures and provide additional support for the stent during the polishing process. The support ends prevent collapse of the stent and excessive polishing of ends of the stent during the polishing process.

The polishing process can be additionally facilitated by ultrasonically vibrating the abrasive media and elevating the pressure of the abrasive media as it flows through the fixture and adjacent surfaces of the stent. If it is desired that the stent be provided with a streamlined contour which is not biased in any one direction, the stent can be removed and reoriented within the fixture for polishing in a reverse direction or the fixture can be disconnected from the source of abrasive media, rotated 180° and recoupled to the source of abrasive media for polishing in a reverse direction. Once the polishing process is completed, the cylindrical support ends are removed from the stent. The stent is then ready for implantation within a body lumen with such finely polished surfaces that restenosis and thrombus are minimized.

OBJECTS OF THE INVENTION

Accordingly, a primary object of the present invention is to provide a method for polishing surfaces of a radially expandable surgical stent which includes flowing a fluid abrasive media adjacent surfaces of the stent to be polished until the stent exhibits a desired finish.

Another object of the present invention is to provide a method for streamlining surfaces of a radially expandable surgical stent by flowing fluid abrasive media adjacent surfaces of the stent to be streamlined.

Another object of the present invention is to provide a method for polishing a radially expandable surgical stent which can polish multiple stents simultaneously.

Another object of the present invention is to provide a fixture for a radially expandable surgical stent polishing process which holds and supports the stent while fluid abrasive media is flowed adjacent surfaces of the stent and which can be easily loaded and unloaded with stents to be polished.

Another object of the present invention is to provide a fixture for a stent polishing process which restricts fluid abrasive media flow to the surfaces forming the inner diameter of the stent.

Another object of the present invention is to provide a fixture for a stent polishing process which restricts fluid abrasive media flow to the surfaces forming the outer diameter of the stent.

Another object of the present invention is to provide a stent polishing fixture which can be readily attached to honing equipment which uses elevated pressure fluid abrasive media and ultrasonic vibration of the fluid abrasive media and directs the fluid abrasive media through the fixture.

Another object of the present invention is to provide a surgical stent which minimizes medical complications such as restenosis and thrombus adjacent the stent.

Another object of the present invention is to provide a radially expandable surgical stent which has a finish smoothness which minimizes medical complications such as restenosis and thrombus adjacent the stent when the stent is implanted within an artery or other body lumen.

Another object of the present invention is to provide a surgical stent which can support a body lumen while minimizing disruption of flow of bodily fluids through the lumen.

Another object of the present invention is to provide a surgical stent which is reversible and can be implanted in two distinct orientations rotated 180° from each other without altering performance of the surgical stent.

Another object of the present invention is to provide a surgical stent which features an inner surface which has edges with greater radii of curvature than radii of curvature of outer edges bordering an outer surface of segments of the stent, such that disruption to blood flow within a body lumen in which the stent is implanted is minimized and the outer surface of the stent is securely held adjacent a wall of the lumen.

Other further objects of the present invention will become apparent from a careful reading of the included description and claims and from a review of the drawing figures.

DESCRIPTION OF THE PREFERRED EMBODIMENT

Referring to the drawings, wherein like reference numerals represent like parts throughout the various different drawing figures, reference numeral 10 is directed to a radially expandable surgical stent (FIG. 1) which has been fitted with non-radially expandable cylindrical support ends 20 at each end of the stent 10. Surfaces of the stent 10 forming an inner diameter of the stent 10 are polished by placing the stent 10 within a stent interior polishing fixture 100 (FIGS. 3–6) and flowing fluid abrasive media M through the fixture 100 with the stents 10 therein. A stent exterior polishing fixture 200 (FIGS. 7–9) is also provided which is configured to polish surfaces of the stent 10 forming an outer diameter of the stent 10 by flowing the abrasive media M adjacent the exterior surfaces of the stent 10. The abrasive media M not only polishes surfaces of the stent 10 but also alters a cross-sectional contour of stent segments 40 (FIGS. 10–15) such that an inner surface 44 is streamlined to minimize disruption of bodily fluid flow passing over the inner surface 44 when the stent 10 is implanted within a body lumen L (FIGS. 16 and 18) after removal of the cylindrical support ends 20.

The fixtures 100, 200 and other details of the polishing method of this invention can be altered to polish surfaces of the stent 10 in various different manners and also to alter a contour of surfaces of the stent 10, such as to streamline surfaces of the stent 10, to cause surface details of the stent 10 to match any of a variety of different desired contours and with a variety of different finish smoothnesses. However, a preferred contour for the stent 10 and stent segments 40 (FIG. 11) of an alternative stent 30, having slightly differently configured stent segments 40 than the circumferential elements 12 and axial elements 14 of the stent 10 (FIGS. 1 and 2), is described in detail. By altering the polishing methods discussed below, stents having different contour characteristics could similarly be generated.

Figure 11:
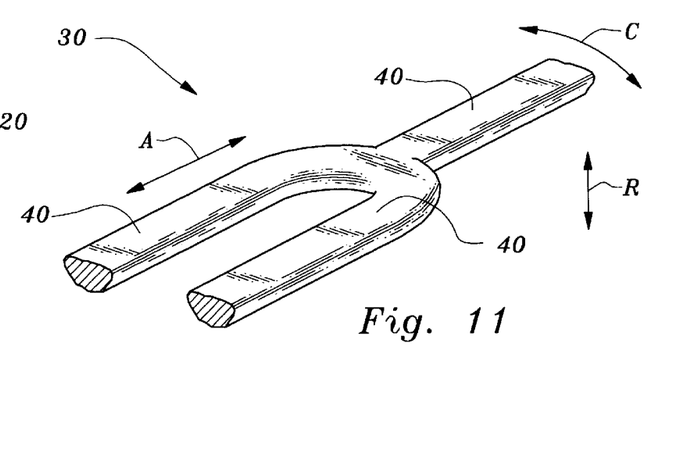
FIG. 11 is a perspective view of that which is shown in FIG. 10 after polishing of surfaces of the stent has been completed according to this invention.
Figure 12:
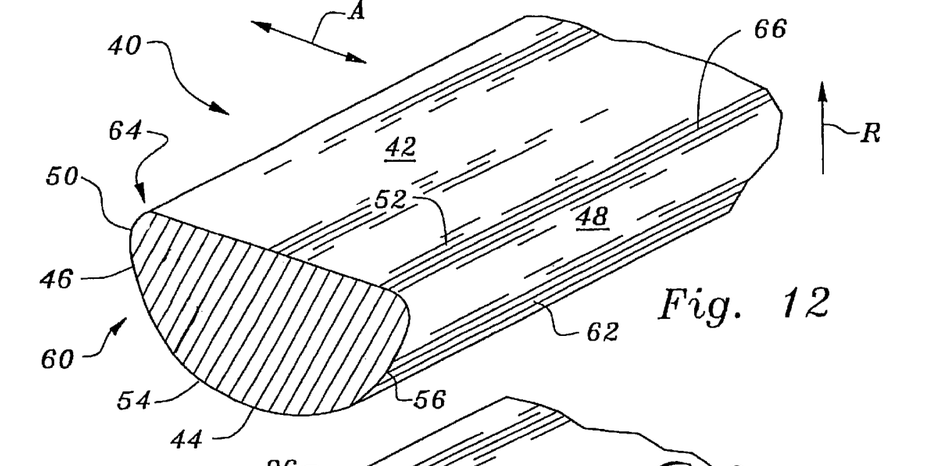
FIG. 12 is a perspective view of a portion of that which is shown in either the stent of FIG. 11 or the stent of FIGS. 1 and 2 revealing in greater detail the exact streamlined contour of the segments of the stent after the polishing method of this invention has been completed.

In essence, and with particular reference to FIGS. 11 and 12, the cross-sectional contour of each stent segment 40 is described, whether the stent segment 40 is taken from the stent 10 or from the alternative stent 30. Each stent segment 40 is an elongate construct of substantially constant cross-sectional generally rectangular form, having an outer surface 42 opposite an inner surface 44. Two lateral side surfaces including a leading surface 46 and a trailing surface 48 extend between the inner surface 44 and the outer surface 42. The inner surface 44 is provided with an inner leading edge 54 and an inner trailing edge 56 which are defined by an inner leading curve 60 and an inner trailing curve 62, respectively, with sufficiently high radii of curvature 70, 72 (FIG. 15) that the inner surface 44 is highly streamlined between the inner leading edge 54 and the inner trailing edge 56.

Figure 18:
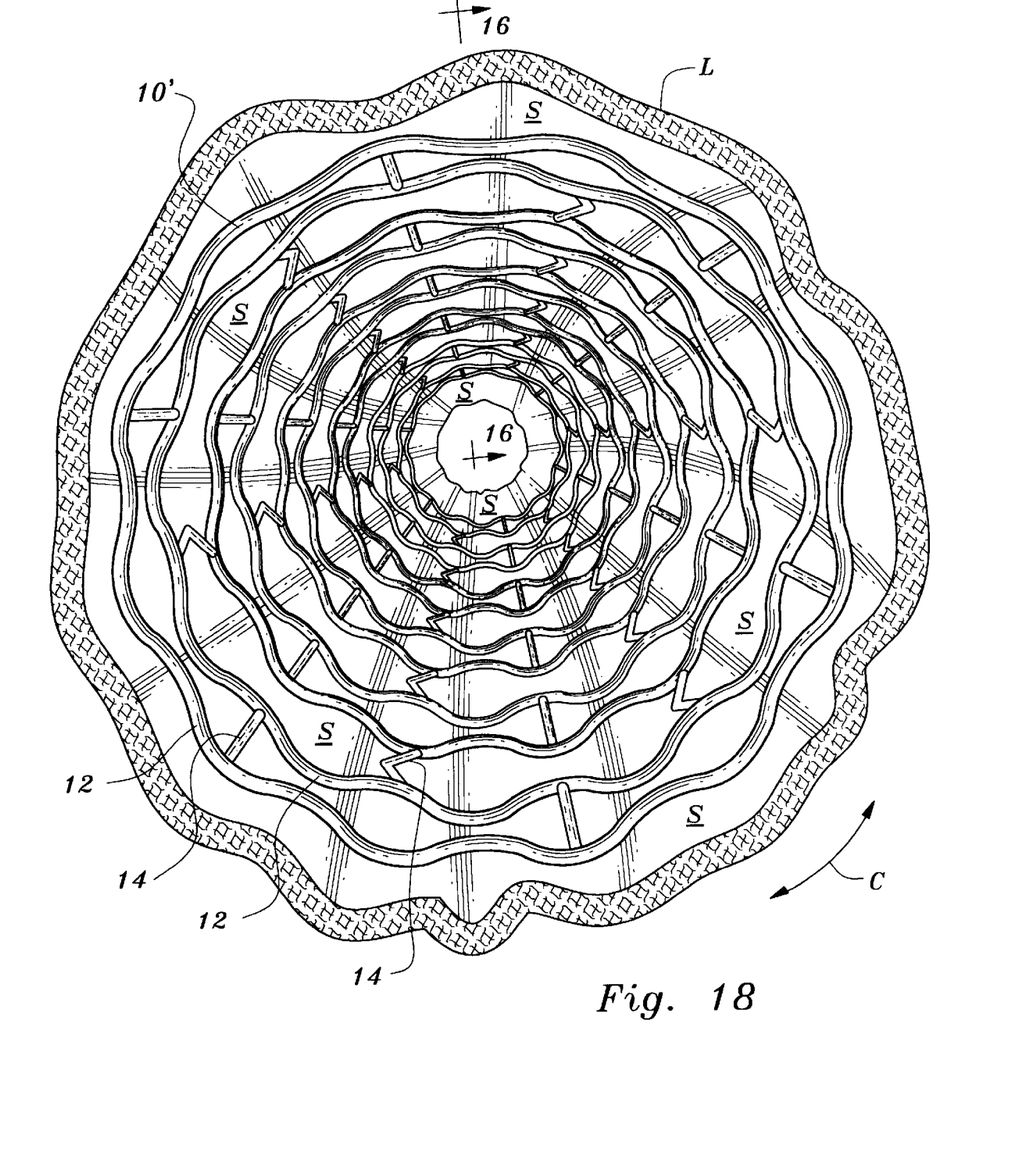
FIG. 18 is a full sectional perspective end view of the polished radially expandable surgical stent in position within a body lumen and radially expanded therein.

The outer surface 42 extends between two side edges including an outer leading edge 50 and an outer trailing edge 52. The outer leading edge 50 is defined by an outer leading curve 64 and the outer trailing edge 52 is defined by an outer trailing curve 66. The outer leading curve 64 and outer trailing curve 66 have radii of curvature 74, 76 (FIG. 15) which are less than the radii of curvature 70, 72 of the inner leading curve 60 and the inner trailing curve 62 (FIG. 12). The stent segment 40 thus has a contour which presents a highly streamlined gradually curving surface for passage of bodily fluid B (FIG. 16) there over and the outer surface 42 presents a more abrupt contour for secure positioning adjacent an inner surface S of the body lumen L (FIGS. 16 and 18).

Before polishing, the stent segments 40' (FIG. 14) of the unpolished stent 10 or alternative stent 30' have planar parallel inner and outer surfaces 44', 42' and planar parallel leading and trailing surfaces 46', 48' perpendicular to the surfaces 44', 42'. The stent segments exhibit abrupt edges 50', 52', 54', 56' between adjacent surfaces 42', 44', 46', 48'. Roughness areas R are located on the surfaces 42', 44', 46', 48'. After polishing, the stent segments 40 (FIG. 12) have greater surface smoothness and a cross-sectional contour which is more streamlined than the stent segment 40'. Specific details of the geometry and other features of the polished and streamlined stent 10 and its alternatives are incorporated by reference from U.S. patent application Ser. No. 08/839,434, filed on Apr. 10, 1997, entitled "SURGICAL STENT HAVING A STREAMLINED CONTOUR," now U.S. Pat. No. 5,718,713.

In use and operation, when a stent 10 featuring stent segments 40 of this invention is implanted into a lumen L (FIGS. 16 and 18) with the stent segments 40 embedding slightly into the inner surface S of the lumen L and supporting the lumen L, blood/fluid flow B is only slightly disrupted and restenosis and plaque buildup is minimized. When prior art stents are implanted (FIG. 17) stent segments 40 having more abrupt contours cause disruption in the blood/fluid flow B producing eddies E which further disrupt blood/fluid flow B and encourage the formation of plaque P, leading to restenosis, along the inner surface S at various locations along the inner surface S. Thrombus H is also stimulated by irregularities in surface finish exhibited by stent segments 40' of prior art stents.

Figure 16:
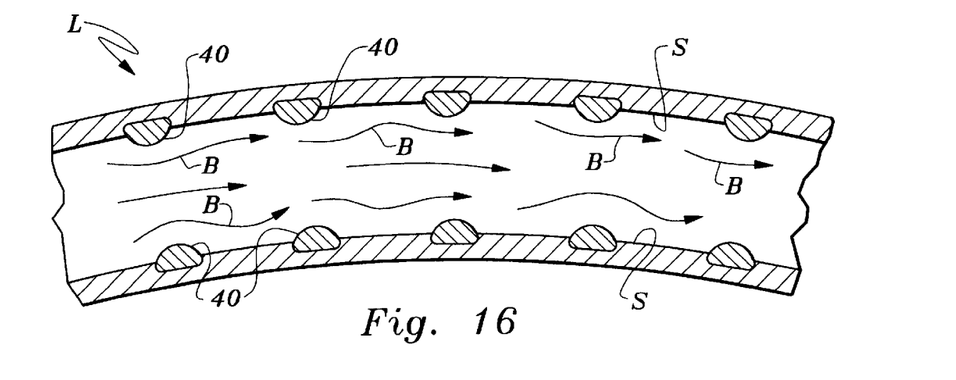
FIG. 16 is a full sectional view taken along lines 16—16 of FIG. 18 and showing a body lumen with a stent, polished according to this invention, located within the body lumen and radially expanded within the body lumen to support walls of the lumen.

With reference particularly to FIGS. 12 and 16, because the leading curves 60, 64 generally match the contour of the trailing curves 62, 66 of each stent segment 40, the stent 10 featuring the stent segment 40 can be reversed 180° with similar function in either orientation. Alternatively, should maximum streamlining of the stent segment 40 be desired, the inner surface 44 can be provided with a more airfoil-like asymmetrical contour which does not provide the leading surface 46 and trailing surface 48 as mirror images of each other, but rather provides the leading surface 46 with a smaller radius of curvature and the trailing surface 48 with a larger radius of curvature or a tapering gradual slope, somewhat analogous to that of a tear drop in cross-section. Such an asymmetrical surgical stent would necessarily only benefit from its form when implanted in a particular direction with regard to blood/fluid flow B through the lumen L.

Having thus described in detail the preferred contour and finished smoothness for the stent 10, it should be apparent that should different finished smoothnesses be desired, for various different purposes, various different curvatures and measurements of the contour of the stent 10 could be similarly provided. This is particularly true when utilizing the polishing method disclosed below. To accomplish polishing and streamlining of the stent 10 to exhibit the contour discussed above, or any other desired contour, the following method is utilized with the apparatus discussed in detail below.

Before polishing the stent 10 according to the method of this invention, the stent 10 is preferably slightly modified to provide additional support to the stent 10 during the polishing process. Specifically, cylindrical support ends 20 are attached to each end of the stent 10. Each cylindrical support end 20 is a cylindrical hollow substantially rigid construct preferably formed from the same material with which the circumferential elements 12 and axial elements 14 of the stent 10 are formed. Each cylindrical support end 20 includes an outer edge 22 on an end of the cylindrical support end 20 most distant from the stent 10 and an inner edge 24 opposite the outer edge 22 and adjacent the stent 10.

A plurality of ties 25 extend from the inner edge 24 to the portions of the stent 10 adjacent to each cylindrical support end 20. The ties 25 are preferably linear elongate segments of the stent 10 which are oriented in an axial direction (along arrow A of FIGS. 1 and 2) and are colinear with axial elements 14 adjacent to the cylindrical support ends 20. Preferably six ties 25 extend between the inner edge 24 and the portions of the stent 10 adjacent the cylindrical support ends 20. Each tie 25 includes an outer end 26 adjacent the inner edge 24 and an inner end 28 opposite the outer end 26 and attached to the end of the stent 10 adjacent the cylindrical support end 20.

The cylindrical support ends 20 can either be attached to the ends of the stent 10 before the polishing process or the cylindrical support ends 20 can be formed along with other portions of the stent 10 originally so that the cylindrical support ends 20 are attached to the stent 10 at all times up until the polishing process is completed. After the polishing process is completed, the cylindrical support ends 20 are removed from ends of the stent 10 along with the ties 25, providing the stent 10' (FIG. 18) in the desired configuration for implantation within a body lumen L.

The cylindrical support ends 20 are not radially expandable. Thus, the cylindrical support ends 20 help support the stent 10 during the polishing process and prevent the stent 10 from being prematurely radially expanded. Additionally, the cylindrical support ends 20 provide a leading edge for the stent 10 during the polishing process and reduce a risk that abrasive media M flowing along surfaces of the stent 10 will cause circumferential elements 12 at ends of the stent 10 to be collapsed or to otherwise collapse the stent 10 axially (along arrow A of FIGS. 1 and 2) due to the added rigidity of the stent 10 when the cylindrical support ends 20 are attached thereto. Preferably, inner and outer diameters of the cylindrical support ends 20 match inner and outer diameters of the stent 10.

Figure 1:
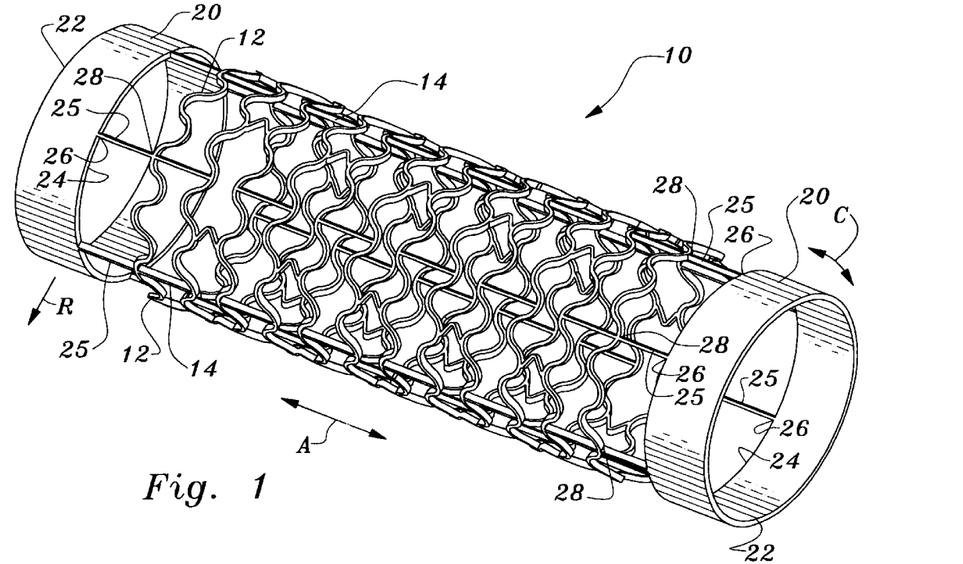
FIG. 1 is a perspective view of a radially expandable surgical stent with cylindrical support ends located adjacent each end of the stent, such that the stent is ready to be placed within a fixture for polishing of surfaces of the stent. The stent is shown with circumferential elements radially expanded to make surfaces of the stent more readily discernible. However, the circumferential elements of the stent would in fact be not radially expanded when attached to the cylindrical support ends.
Figure 2:
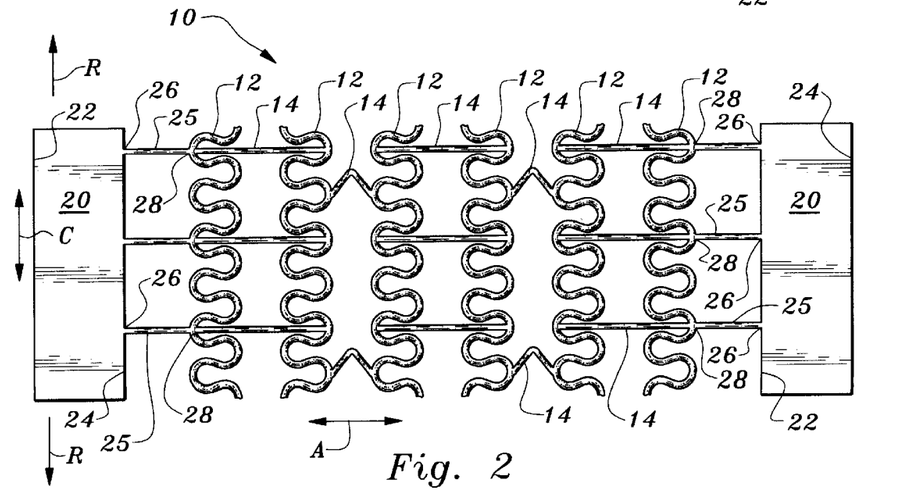
FIG. 2 is a cylindrical projection of a portion of that which is shown in FIG. 1 with the circumferential elements shown not radially expanded as the circumferential elements would appear when attached to the cylindrical support ends and during the polishing process of this invention.

With reference to FIG. 2, further details of the stent 10 with the cylindrical support ends 20 attached thereto are provided. Reference arrow C indicates a circumferential direction and reference arrows R represent the radially direction in which the stent 10 is radially expanded after removal of the cylindrical support ends 20 from the stent 10. FIG. 2 shows the circumferential elements 12 in an undulating fashion having not yet been radially expanded, as is the case while the cylindrical support ends 20 are attached thereto. In contrast, FIG. 1 shows the circumferential elements 12 radially expanded to illustrate the difference in the configuration of the stent 10 after radial expansion. The cylindrical support ends 20 would not be attached to other portions of the stent 10 when the stent 10 has been radially expanded, along arrow R. Hence, FIG. 1 is a composite view which would not actually exist, but depicts the configuration of the cylindrical support ends 20 in perspective and a perspective view of the radially expandable surgical stent 10 after it has been radially expanded.

While various different systems could be utilized to effectively flow abrasive media past surfaces of the stent 10 for polishing, a preferred system for effectively flowing the fluid abrasive media M past surfaces of the stent 10, and particularly for polishing surfaces of the stent 10 forming an inner diameter of the stent 10, are provided by the stent interior polishing fixture 100 (FIGS. 3–6). The stent interior polishing fixture 100 is a rigid construct configured to provide a means to hold a series of stents 10 motionless and provide conduits for fluid abrasive media M to flow adjacent surfaces of the stent 10 forming an inner diameter of the stent 10. The interior polishing fixture 100 includes a top 102 parallel to and spaced from a bottom 104. Four parallel sides 106 are oriented perpendicular to the top 102 and bottom 104. Hence, the top 102, bottom 104 and sides 106 form an orthorhombic rigid mass of solid material.

A series of bores 108 pass from the top 102 through to the bottom 104 of the fixture 100. Preferably, each bore 108 is cylindrical in form and passes along a line perpendicular to the top 102 and the bottom 104. Preferably, the bores 108 have a diameter which is similar to the inner diameter of the stent 10. The fixture 100 is preferably not formed from a single unitary mass of material but rather from a series of rigid plates including two end plates 120 and a plurality of mid-plates 140 sandwiched between the two end plates 120.

Each of the plates 120, 140 is securely held together with closure bolts 112 passing through the interior polishing fixture 100 in an orientation parallel to the top 102 and bottom 104 of the fixture 100 and perpendicular to adjacent surfaces of the end plates 120. Preferably, two closure bolts 112 are provided passing through the fixture 100 at locations which prevent the closure bolts 112 from intersecting with the bores 108. Each closure bolt 112 includes a head 114 on an end of each bolt 112 opposite a threaded tip 116. Wing nuts 118 are provided which thread onto the threaded tip 116. The closure bolts 112 can pass through the plates 120, 140 forming the fixture 100 with the head 114 of each closure bolt 112 adjacent one of the end plates 120 and the wing nuts 118 threaded onto the closure bolts 112 adjacent the opposite end plate 120. By tightening the wing nuts 118 against the end plate 120, the plates 120, 140 are securely sandwiched together without motion.

The bores 108 are aligned to pass between an end plate 120 and a mid-plate 140 or between two adjacent mid-plates 140. In this way, access is provided to a cylindrical chamber 135 within the bore 108 when the plates 120, 140 of the interior polishing fixture 100 are separated away from each other. Preferably, three mid-plates 140 are provided between the two end plates 120 and five bores 108 are provided at each transition between an end plate 120 and an adjacent mid-plate 140 and between adjacent mid-plates 140, such that a total of twenty bores 108 are provided passing from the top 102 to the bottom 104 of the interior polishing fixture 100.

Figures 3, 4, 5:
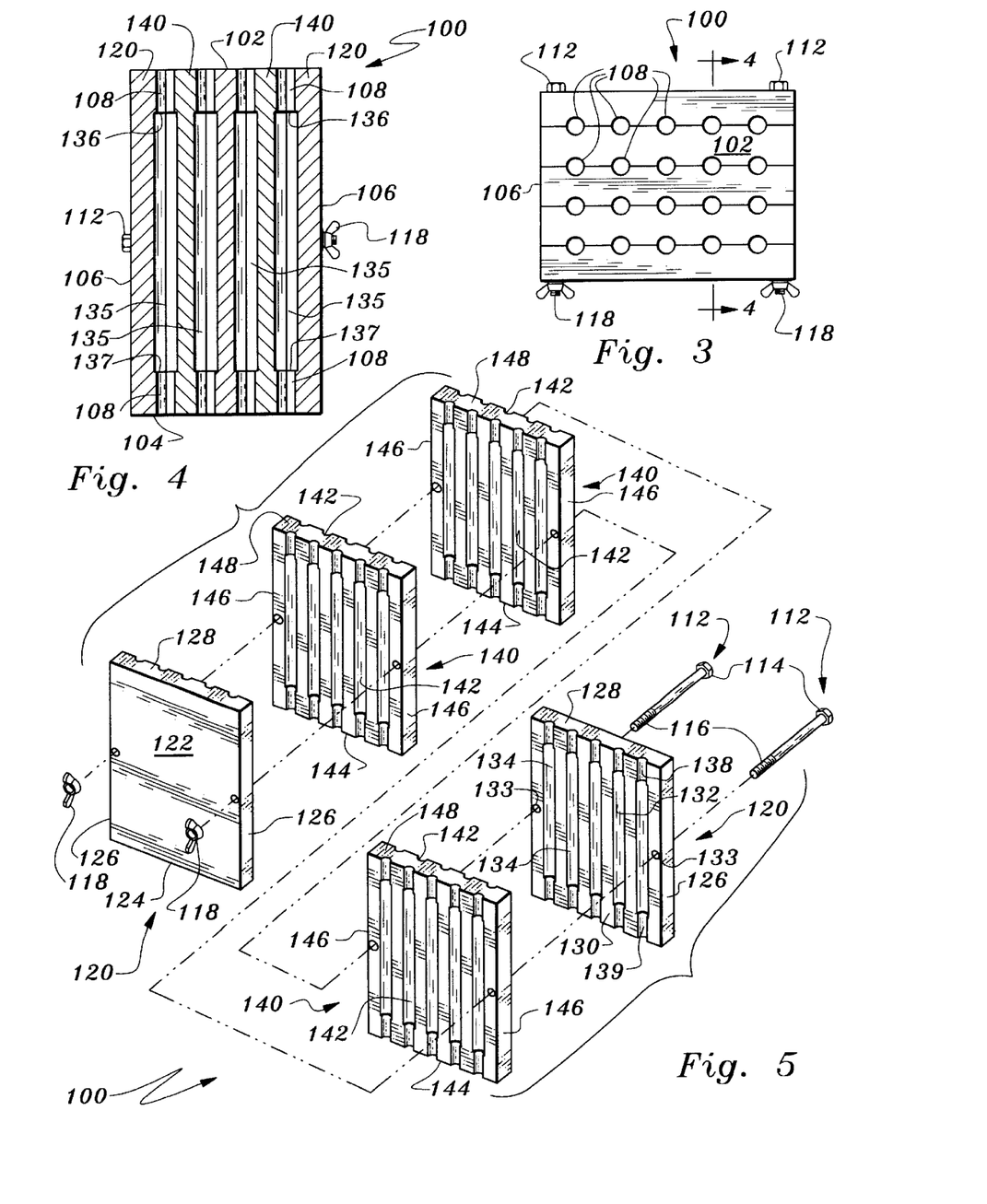
FIG. 3 is a top plan view of a stent interior surface polishing fixture for use according to the polishing method of this invention.
FIG. 4 is a full sectional view of that which is shown in FIG. 3 taken along lines 4—4 of FIG. 3.
FIG. 5 is a perspective exploded parts view of that which is shown in FIG. 3 revealing how separate plates of the fixture are coupled together to form the fixture of FIG. 3.

With particular reference to FIG. 5, specific details of each end plate 120 are provided. Each end plate 120 is a unitary rigid mass of material which forms a portion of the interior polishing fixture 100. Each end plate 120 includes an outer surface 122 which does not include any portion of a bore 108 thereon. Each end plate 120 includes a bottom 124 parallel to and spaced from a top 128 which form portions of the top 102 and bottom 104 of the interior polishing fixture 100. Each end plate 120 also includes lateral sides 126 parallel to each other and oriented perpendicular to the bottom 124 and top 128.

An inner surface 130 is provided on the side of the end plate 120 opposite the outer surface 122. This inner surface 130 is similarly formed on each of the two end plates 120. The inner surface 130 is contoured to include portions of the bores 108 therein. Each inner surface 130 includes a flat plane 132 defining portions of the inner surface 130 which do not include portions of the bores 108 therein. Two bolt holes 133 pass through the inner surface 130 and entirely through to the outer surface 122 of each end plate 120. The bolt holes 133 have a diameter which accommodates passage of the closure bolts 112 there through. The bolt holes 133 are preferably located at a position intermediate between the bottom 124 and top 128 of the end plate 120 and between a lateral side 126 of the end plate 120 and a closest bore 108. Alternatively, the bolt holes 133 can be located at any location on the inner surface 130 where the flat plane 132 is provided, rather than a portion of a bore 108.

Each bore 108 includes a void defined by a cylindrical chamber 135 therein. The cylindrical chamber 135 is formed by having a cylindrical chamber wall 134 contoured into the inner surface 130 of each end plate 120. Preferably, with five bores 108 passing between each end plate 120 and an adjacent mid-plate 140, five cylindrical chamber walls 134 are formed in the inner surface 130. The cylindrical chamber wall 134 is semi-cylindrical in form providing exactly one-half of the cylindrical chamber 135. The cylindrical chamber wall 134 does not extend all the way up to the top 128 or to the bottom 124 of the end plate 120. Rather, the cylindrical chamber wall 134 forms an interior detail of one of the bores 108 which does not extend to the top 102 and bottom 104 of the interior polishing fixture 100.

The cylindrical chamber wall 134 preferably has a diameter similar to an outer diameter of the stent 10. The cylindrical chamber wall 134 extends from a top chamber end 136 to a bottom chamber end 137 (FIG. 4). Above the top chamber end 136 a top cylindrical bore wall 138 (FIG. 5) is provided forming a portion of the bore 108 extending from the cylindrical chamber 135 up to the top 102 of the fixture 100. A bottom cylindrical bore wall 139 (FIG. 5) similarly extends from the bottom chamber end 137 to the bottom 104 of the interior polishing fixture 100.

The top cylindrical bore wall 138 and bottom cylindrical bore wall 139 form exactly half of the cylindrical bore 108 leading into and out of the cylindrical chamber 135. The top chamber end 136 and bottom chamber end 137 provide a transition between the larger diameter of the cylindrical chamber 135 and the smaller diameter of the bores 108. With the top chamber end 136 and bottom chamber end 137 spaced apart similar to an axial length of the stent 10, a stent 10 can be located within the cylindrical chamber 135 with the outer diameter of the stent 10 adjacent the cylindrical chamber wall 134 and with the cylindrical support ends 20 of the stent 10 adjacent the top chamber end 136 and bottom chamber end 137. In this position, the inner diameter of the stent 10 is aligned with the bore walls 138, 139 forming the bores 108.

The mid-plates 140 are similar to the end plates 120 except that each mid-plate 140 includes two contoured surfaces 142 each similar in contour to the contour provided by the inner surface 130 of each end plate 120. The mid-plates 140 include a bottom 144 parallel to and spaced from a top 148 with two parallel lateral sides 146 oriented perpendicular to the bottom 144 and top 148.

Figure 6:
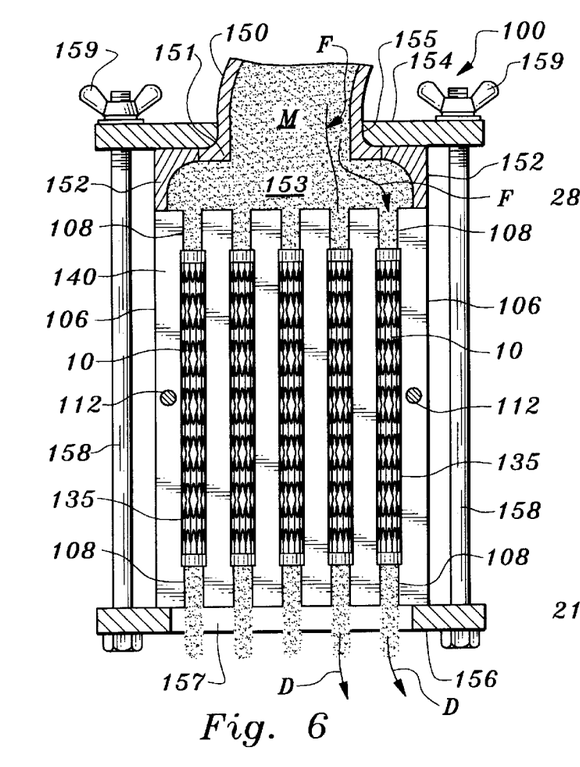
FIG. 6 is a sectional view of the fixture of FIG. 3 with other portions of the honing equipment and fluid abrasive media supply attached to the fixture and revealing how fluid abrasive media is caused to flow through the fixture and adjacent surfaces of the stent forming the inner diameter of the stent.

With particular reference to FIG. 6, other portions of the stent polishing apparatus which attach to the interior polishing fixture 100 are described in detail. A hose 150 is located adjacent the top 102 of the interior polishing fixture 100. The hose 150 provides a source for fluid abrasive media M which can lead from a reservoir up to the top 102 of the fixture 100. A lower end 151 of the hose 150 is located adjacent a manifold plate 152. The manifold plate 152 is a rigid construct which is configured to seal against the top 102 of the fixture 100 with a manifold chamber 153 therein provided in fluid communication with each of the bores 108 in the interior polishing fixture 100. The manifold chamber 153 is also open to the interior of the hose 150 so that fluid abrasive media M can flow through the hose 150, out of the lower end 151 of the hose 150 and into the manifold chamber 153; where it can then flow into each of the bores 108 in the interior polishing fixture 100.

A top clamp plate 154 is located over the manifold plate 152 and secures the manifold plate 152 to the top 102 of the fixture 100. A hose opening 155 is located in the top clamp plate 154 so that the hose 150 can still access the manifold chamber 153. A bottom clamp plate 156 is located adjacent the bottom 104 of the fixture 100. The bottom clamp plate 156 includes a central opening 157 which leaves the bores 108 in the bottom 104 unblocked. A series of clamp bolts 158 with wing nuts 159 pass through the top clamp plate 154 and bottom clamp plate 156 and can be threaded together, drawing the bottom clamp plate 156 and top clamp plate 154 toward each other and securing the manifold plate 152 and hose 150 adjacent the top 102 of the interior polishing fixture 100.

In use and operation, the interior polishing fixture 100 is utilized to polish surfaces forming an inner diameter of the stent 10 in the following manner. Initially, the closure bolts 112 are removed from the fixture 100 and the end plates 120 and mid-plates 140 are each separated from each other. Each cylindrical chamber 135 is then preferably provided with a separate stent 10 and the end plates 120 and mid-plates 140 are placed adjacent each other with the closure bolts 112 in place securing the plates 120, 140 together. The manifold plate 152 is then placed over the top 102 of the fixture 100 with the hose 150 interfacing with the manifold plate 152. The top clamp plate 154 and bottom clamp plate 156 are then oriented over the top 102 and bottom 104, respectively, of the fixture 100 and the wing nuts 159 are tightened to secure the manifold plate 152 and hose 150 in position adjacent the top 102 of the fixture 100.

Fluid abrasive media M is then passed (along arrow F) through the hose 150 into the manifold chamber 153, through the bores 108 and into the cylindrical chamber 135 where the fluid abrasive media M flows adjacent surfaces forming the inner diameter of the stent 10. The media M then flows out of the bores 108 and through the central outflow opening 157 in the bottom clamp plate 156 (along arrow D).

Preferably, the fluid abrasive media M flows through the fixture 100 and past the inner diameter of the stent 10 for a desired amount of time and then the fluid abrasive media M is caused to flow in a reverse direction against the inner diameter of the stent 10. Reversal of flow of the abrasive media M can be accomplished by removing the fixture 100 from the clamp plates 154, 156, reversing the fixture 100 and replacing the fixture 100 within the clamp plates 154, 156 with the top clamp plate 154 and manifold plate 152 adjacent the bottom 104 of the fixture 100. Alternatively, the hose 150 and a source of fluid abrasive media M can be configured to allow flow in both directions through the bores 108 of the fixture 100.

If a streamlined contour is desired for surfaces forming the inner diameter of segments 40 (FIG. 12) forming the stent 10, rather than mere polishing of surfaces of the stent 10, the fluid abrasive media M would be allowed to flow through the fixture 100 for a greater amount of time or the fluid abrasive media M could be provided with particles having a greater amount of abrasiveness. If a streamlined contour of symmetrical form is desired, the amount of time with which the media M flows in a first direction should approximate the amount that it flows in a reverse direction.

Polishing of surfaces of the stent 10 can be further enhanced by ultrasonically vibrating the abrasive media M as the abrasive media M flows through the fixture 100 and adjacent surfaces of the stent 10. Specifically, the hose 150 and a source of fluid abrasive media M on an end of the hose 150 opposite the lower end 151 can be fitted with an ultrasonic vibration generation device which causes high frequency agitation of the fluid abrasive media M as it flows through the fixture 100. Another parameter which can be utilized to enhance the effectiveness of the fluid abrasive media M is to supply the fluid abrasive media M at a pressure greater than atmospheric pressure as the fluid abrasive media M passes through the fixture 100. Such enhanced pressure can be provided with pistons in communication with the fluid abrasive media M or other pumps or other pressure generation means acting on the fluid abrasive media M before or during fluid abrasive media M flow through the hose 150 and into the fixture 100.

The fluid abrasive media M can either exit the bores 108 of the fixture 100 into an atmospheric pressure region without any specific enclosures or it can be fitted with an outlet hose similar to the hose 150 for collection of the fluid abrasive media M. If desired, the fluid abrasive media can oscillate back and forth through the bores 108 rather than flowing continuously in a first direction through the bores 108 and then being reversed in direction to flow in an opposite direction through the bores 108.

Figure 17:
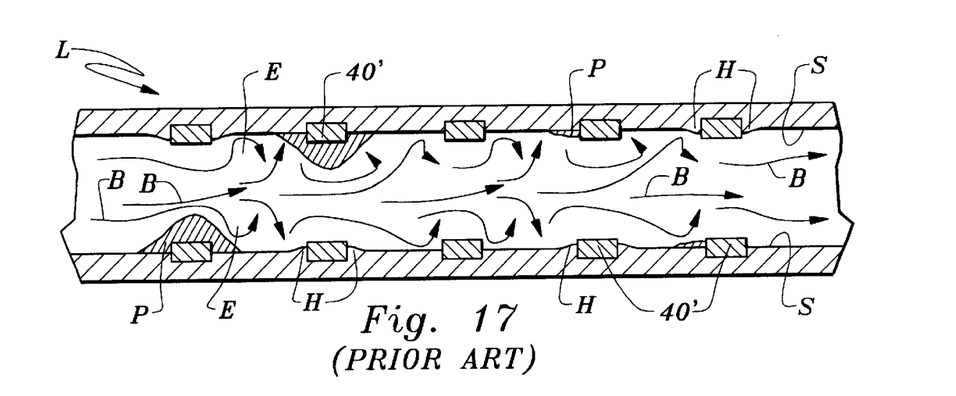
FIG. 17 is a full sectional view of a body lumen with a non-polished or minimally polished radially expandable surgical stent located therein and revealing turbulent blood flow, restenosis and thrombus within the body lumen.

The sizing of the bores 108 to have a similar diameter to the inner diameter of the stent 10 and the chamber 135 to have a similar diameter to the outer diameter of the stent 10 prevents the fluid abrasive media M from flowing past surfaces forming the outer diameter of the stent 10 and maintains surfaces of the stent 10 forming the outer diameter in a substantially unpolished and unstreamlined form. It has been found to be particularly advantageous that the inner diameter of the stent 10 be polished and streamlined such that blood B or body fluids can pass through a lumen L where the stent 10 is located and radially expanded in a manner which decreases turbulence of blood B flowing through the lumen L (FIGS. 16 and 17).

Figure 13:
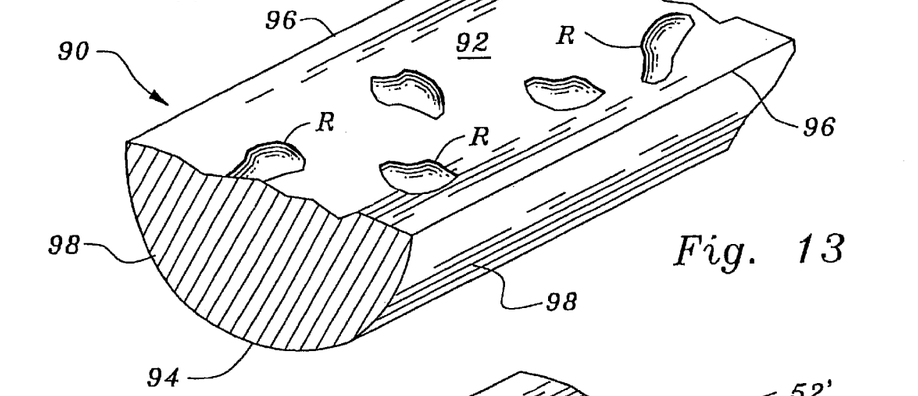
FIG. 13 is a perspective view of a segment of a stent when only the portions of the stent forming the inner diameter of the stent have been polished and with surfaces forming the outer diameter of the stent left unpolished.
Figure 14:
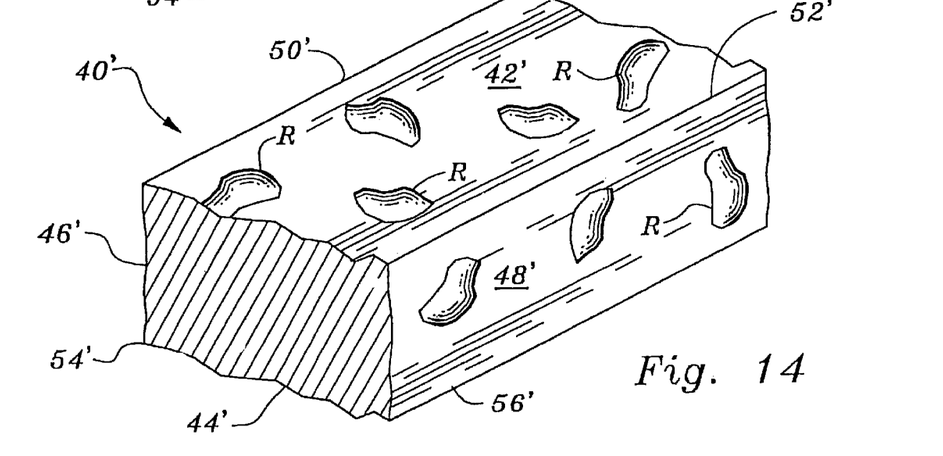
FIG. 14 is a perspective view of a portion of that which is shown in FIG. 10 revealing how the surfaces of the stent exhibit roughness before the polishing method of this invention is performed.

An alternative stent segment 90 is shown in FIG. 13 where only the inner diameter of the stent segment 90 has been polished and streamlined. An outer surface 92 remains substantially planar with outer edges 96 abruptly transitioning to the inner edges 98 leading to the inner surface 94 which has been streamlined. Areas of roughness R can either remain on the outer surface 92 where the stent segment 90 is located adjacent an inner surface S of the lumen L (FIGS. 16 and 17) or be polished merely to remove roughness R but not to streamline or round off edges of the stent segment 90. Such an alternative stent segment 90 would typically result in utilization of the stent interior polishing fixture 100 alone, with little or no utilization of the stent exterior polishing fixture 200 described below.

While various different parameters can be selected in performing the polishing process disclosed herein, it has been found effective and preferable to have abrasive media particle sizes between 0.008 and 0.0003 inches. It has been found preferable to maintain an elevated pressure between 300 and 800 pounds per square inch. An abrasive media M which has been found to be effective is aluminum oxide or silicon carbide. Alternatively, diamond particles could be utilized.

Figure 15:
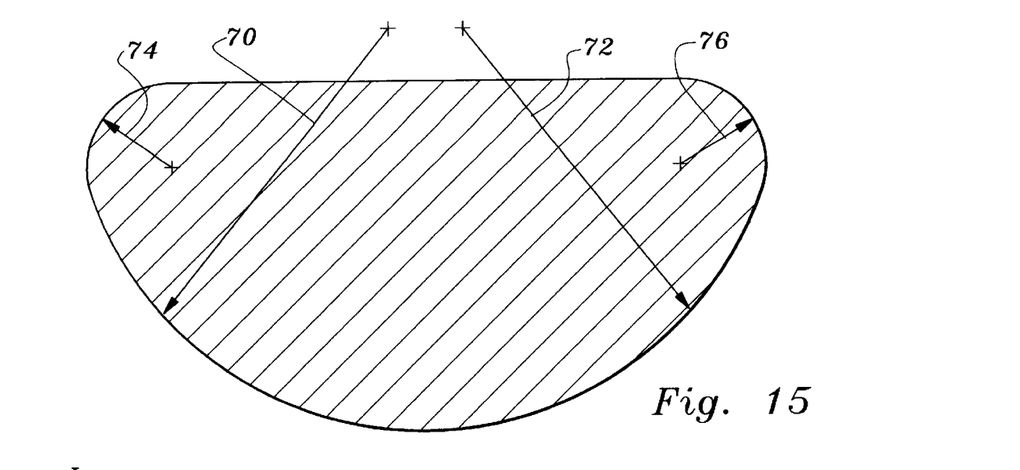
FIG. 15 is a full sectional view of that which is shown in FIG. 12 revealing further details of the streamlined contour of segments of the stent after completion of the polishing method according to this invention.

More specifically, successful tests were run of a fixture 100 similar to that disclosed herein utilizing aluminum oxide with a particle size of 0.0007 inches at a pressure of 500 pounds per square inch with a total process time of thirteen minutes (7.5 minutes each direction) and a desirable surface finish with streamlining of stainless steel stent segments 40 similar to that shown in FIGS. 12 and 15 resulted. In another test, silicon carbide was utilized with a particle size of 0.006 inches at 500 pounds per square inch with a total process time of thirteen minutes and similar contours to those shown in FIGS. 12 and 15 resulted. Specifically, surface roughness R was reduced to elimination of any prominences greater than 5 micro inches above adjacent portions of the surfaces.

Once the stents 10 have been polished by flow of the fluid abrasive media M through the fixture 100, the hose 150 and other apparatus adjacent the fixture 100 are removed and the individual plates 120, 140 are separated from each other for removal of the stents 10 therefrom. The cylindrical end supports 20 are then removed from the stents 10, providing a polished stent 10' (FIG. 18) which is now ready for implantation and radial expansion within a body lumen L as is known in the art.

Figure 7:
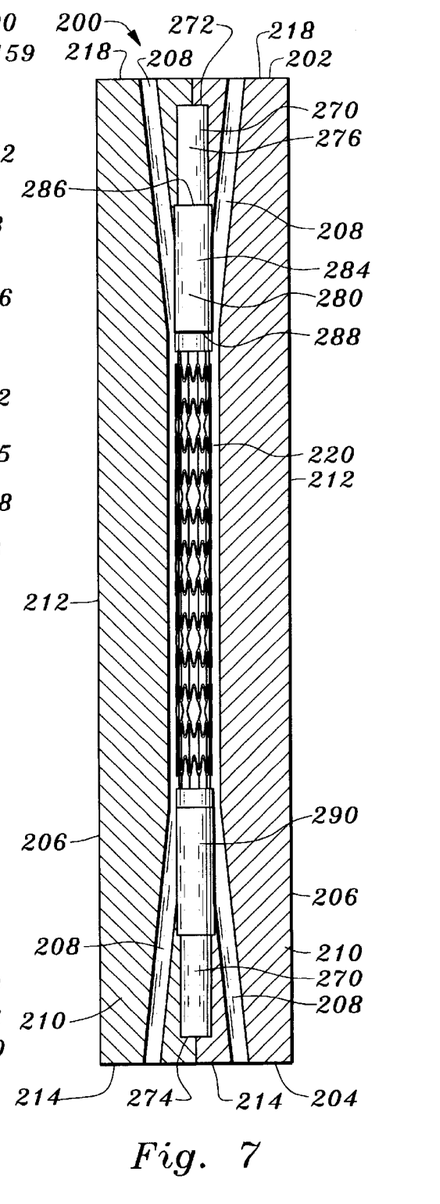
FIG. 7 is a full sectional view taken along lines 7—7 of FIG. 8 and revealing details of a polishing fixture for polishing exterior surfaces of a stent.
Figure 8:
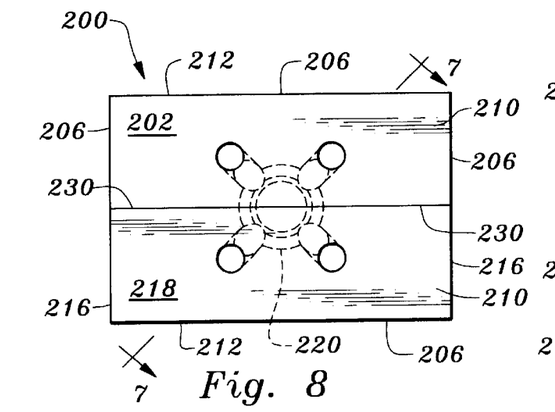
FIG. 8 is a top plan view of the stent exterior surface polishing fixture with interior details thereof shown with broken lines to show locations of voids within the fixture.
Figure 9:
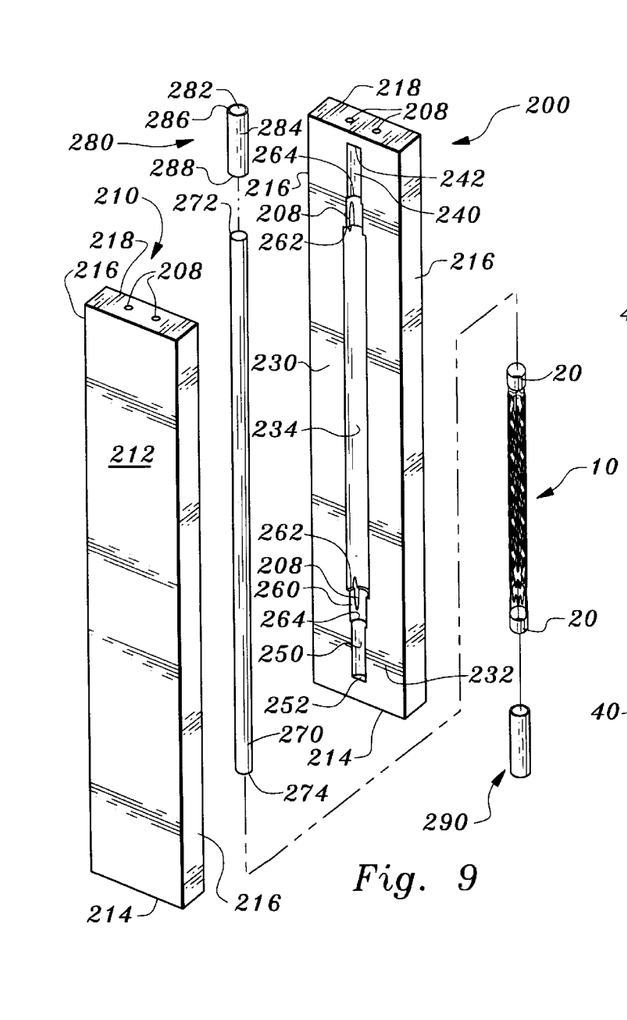
FIG. 9 is a perspective exploded parts view of that which is shown in FIGS. 7 and 8 revealing how the stent is oriented within the stent exterior surface polishing fixture for polishing of exterior surfaces forming the outer diameter of the stent.
Figure 10:
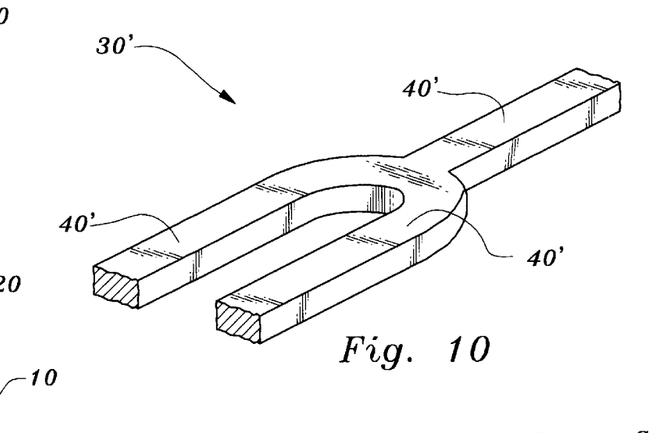
FIG. 10 is a perspective view of a portion of an alternative stent before any polishing of surfaces of the stent has occurred.

With particular reference to FIGS. 7–9, details of the stent exterior polishing fixture 200, which is configured to particularly provide polishing for surfaces forming an outer diameter of the stent 10, are described in detail. The stent exterior polishing fixture 200 is shown in FIGS. 7–9 as having a void therein for supporting only a single stent 10 for polishing therein. However, the exterior polishing fixture 200 could be modified to include multiple separate voids and multiple separate plates as in the case of the interior polishing fixture 100 such that multiple stents 10 can be polished simultaneously within the stent exterior polishing fixture 200. For convenience, the details of the stent exterior polishing fixture 200 will be described for an embodiment where only a single void for a single stent 10 is provided within the stent exterior polishing fixture 200.

The exterior polishing fixture 200 is a solid rigid mass of material having a top 202 parallel to and spaced from a bottom 204 with sides 206 extending perpendicularly between the top 202 and the bottom 204. Multiple slanted bores 208 pass through the top 202 and bottom 204 and communicate together such that fluid abrasive media M can flow entirely through the fixture 200 from the top 202 to the bottom 204, in a manner similar to that described above with respect to the interior polishing fixture 100.

The exterior polishing fixture 200 is formed from two identical end plates 210 having an outer surface 212 extending perpendicularly between a bottom 214 and a top 218 which form portions of the bottom 204 and top 202, respectively, of the exterior polishing fixture 200. A lateral surface 216 defines surfaces of the end plate 210 perpendicular to the bottom 214 and top 218 and also perpendicular to the outer surface 212.

A cylindrical recess 220 somewhat analogous to the cylindrical chamber 135 in the interior polishing fixture 100 is located within the exterior polishing fixture 200 in fluid communication with the slanted bores 208. The cylindrical recess 220 is formed between the two end plates 210 such that the cylindrical recess 220 is in fact formed in an inner surface 230 parallel to and spaced from the outer surfaces 212 of the two end plates 210. Each inner surface 230 includes a flat plane 232 defining portions of the inner surface 230 where the cylindrical recess 220 is not located and a cylindrical recess wall 234 defining exactly one-half of the cylindrical recess 220. The cylindrical recess wall 234 is preferably semi-cylindrical in form and has a diameter greater than an outer diameter of the stent 10.

A top blind bore 240 extends up from the cylindrical recess 220 between the multiple slanted bores 208. The top blind bore 240 extends up to a top bore wall 242 perpendicular to the cylindrical recess wall 234 of the cylindrical recess 220. A bottom blind bore 250 similar to the top blind bore 240 but below the bottom of the cylindrical recess 220 is also located within the exterior polishing fixture 200. The bottom blind bore 250 includes a bottom bore wall 252 parallel to the top bore wall 242.

Between the top bore wall 242 and bottom bore wall 252 and the cylindrical recess wall 234 two similar collar support regions 260 are located. The top blind bore 240, bottom blind bore 250 and two collar support regions 260 are each cylindrical in form but exhibit different diameters extending away from a central axis common with the cylindrical recess 220. A recess edge 262 defines a diameter transition between the cylindrical recess wall 234 and the two collar support regions 260. A bore edge 264 is located at a transition between the collar support regions 260 and the two blind bores 240, 250.

Preferably, the slanted bores 208 extend from the top 202 and the bottom 204 up into the collar support regions 260. Preferably, two slanted bores 208 are located within each end plate 210 such that a total of four slanted bores 208 pass from the top 202 into the cylindrical recess 220 and four slanted bores 208 pass from the bottom 204 into the cylindrical recess 220.

The cylindrical recess wall 234 has a diameter greater than an outer diameter of the stent 10. The collar support regions 260 have a diameter similar to an outer diameter of the stent 10. The blind bores 240, 250 have a diameter similar to an inner diameter of the stent 10.

A shaft 270 is provided having a length similar to a distance between the top bore wall 242 and the bottom bore wall 252 and having a diameter similar to a diameter of the blind bores 240, 250 and the inner diameter of the stent 10. Thus, the stent 10 can be placed on the shaft 270 with the inner diameter of the stent 10 adjacent the shaft 270. The shaft 270 includes a top end 272 parallel to and spaced from a bottom end 274 with a cylindrical surface 276 sized to be located adjacent the inner diameter of the stent 10. The shaft 270 is located within the exterior polishing fixture 200 with the top end 272 within the top blind bore 240 and the bottom end 274 within the bottom blind bore 250 when the exterior polishing fixture 200 is in use for polishing exterior surfaces of the stent 10.

An upper collar 280 is provided having an inner surface 282 with a diameter similar to a diameter of the cylindrical surface 276 of the shaft 270. The upper collar 280 includes an outer surface 284 with a diameter similar to a diameter of the collar support regions 260 and the outer diameter of the stent 10. The upper collar 280 is a hollow cylindrical rigid construct extending from a circular top edge 286 to a circular bottom edge 288. The upper collar 288 has a length between the top edge 286 and the bottom edge 288 which causes the upper collar 280 to be longer than a distance within each collar support region 260 from the recess edge 262 to the bore edge 264. Thus, when the upper collar 280 is located on the shaft 270 within the fixture 200 the upper collar 280 extends down into the cylindrical recess 220 somewhat. A lower collar 290 is provided with a form similar to that of the upper collar 280.

Preferably, the cylindrical recess 220 has a length between the recess edges 262 which is slightly greater than a length of the stent 10 and actually includes a length of the stent 10 and a length of portions of each collar 280, 290 which extend from the recess edges 262 into the cylindrical recess 220. Thus, when the shaft 270 is located within the exterior polishing fixture 200 with the top end 272 within the top blind bore 240 and the bottom end 274 within the bottom blind bore 250 and with the collars 280, 290 located upon the shaft 270 and within the collar support regions 260 (as shown in FIG. 7), sufficient space is provided between the upper collar 280 and the lower collar 290 for the stent 10 to be placed over the shaft 270 and between the upper collar 280 and the lower collar 290 without any axial motion of the stent 10 between the collars 280, 290 within the exterior polishing fixture 200 allowed.

Preferably, the shaft 270, upper collar 280 and lower collar 290 are each separate pieces so that the stent 10 can be easily placed upon the shaft 270 with the collars 280, 290 also on the shaft 270 adjacent ends of the stent 10. The shaft 270, collars 280, 290 and stent 10 can then be simultaneously placed together within the cylindrical recess 220, top blind bore 240, bottom blind bore 250 and collar support regions 260 as the two end plates 210 of the exterior polishing fixture 200 are closed together.

Preferably, closure bolts similar to the closure bolts 212 of the interior polishing fixture 100 are utilized to secure the end plates 210 together. Also, a clamping system, manifold plate and hose are provided in a manner similar to that discussed above with respect to the interior polishing fixture 100 to deliver fluid abrasive media M through the slanted bores 208 and into the cylindrical recess 220.

Because the cylindrical recess 220 has a diameter greater than the outer diameter of the stent 10, and because the shaft 270 prevents fluid abrasive media M from flowing adjacent interior surfaces of the stent 10, the fluid abrasive media M is caused to flow exclusively over surfaces of the stent 10 forming the outer diameter of the stent 10. As with the use of the interior polishing fixture 100 discussed above, various different fluid abrasive media M can be utilized with different pressures, durations, particle sizes, and ultrasonic vibration, as required to produce a desired finished surface for outer surfaces of the stent 10. Preferably, the outer diameter of the stent 10 is polished to have a smooth surface but is not significantly streamlined. Rather the stent segments 40 are provided with relatively abrupt leading and trailing edges 50, 52 (FIGS. 12 and 15) so that the stent 10 will remain securely in place when radially expanded within a body lumen L, without sliding along the inner surface S of the body lumen L, but preferably does not have patches of roughness R (FIGS. 13 and 14) which might cause irritation of the body lumen L and lead to thrombus, restenosis or other detrimental complications.

Preferably, the slanted bores 208 enter into the cylindrical recess 220 at a location where the upper collar 280 and lower collar 290 are provided. Thus, extreme upper portions of the cylindrical recess 220 provide a zone where the fluid abrasive media M can flow laterally between adjacent slanted bores 208 and fill the cylindrical recess 220 before the fluid abrasive media M flows down to the cylindrical recess 220 and comes into contact with surfaces of the stent 10 forming the outer diameter of the stent 10. In this way, all locations within the cylindrical recess 220 are provided with fluid abrasive media M for polishing, without any vacant regions in the abrasive media M flow.

While the exterior polishing fixture 200 has been separately disclosed and described with respect to a preferred interior polishing fixture 100, it is understood that a fixture could be provided which allows abrasive media M to flow simultaneously adjacent an inner diameter and an outer diameter of the stent 10 such that a single composite fixture rather than two separate fixtures would be provided. The benefits of such a composite fixture, including overall simplification of the stent polishing process would necessarily be compared with the added complexity of such a fixture and difficulties associated with securing the stent 10 in position within such a fixture and adequately supporting the stent 10 such that the stent 10 is not damaged during high pressure flow of the abrasive media M adjacent surfaces of the stent 10.

Other further modifications to the fixtures 100, 200 and the polishing process could also be resorted to without departing from the scope of the invention. The specific embodiments disclosed herein are provided merely by way of example and to provide a best mode and preferred embodiment for practicing this invention and should not be considered as further limiting the claims included herein below.

What is claimed is:

1. A fixture for supporting a cylindrical radially expandable surgical stent during a stent polishing procedure which uses contact of a fluid abrasive media with the surfaces of the stent in a honing process to polish the stent, the fixture comprising:

a rigid mass having a top and a bottom;

at least one bore in said mass passing from said top to said bottom, each said at least one bore configured to allow the abrasive media to flow therethrough;

a void located within each said at least one bore and between a top and a bottom of said bore and having a width similar to an outer diameter of the stent and a length similar to a length of the stent; and said respective bore having a width adjacent to upper and lower ends of said respective void less than the outer diameter of the cylindrical radially expandable surgical stent, such that the stent cannot pass out of said void and into said respective bore, said bore having a substantially circular cross-section adjacent said void with a diameter similar to an inner diameter of the stent, such that the fluid abrasive media passing through said bore and into said void is shielded from hitting ends of the stent but rather flows adjacent to surfaces of the stent forming the inner diameter of the stent.

2. The fixture of claim 1 wherein each said void aligns a central axis of the cylindrical radially expandable surgical stent with a direction of abrasive media flow through a respective said void within a respective said bore of said rigid mass.

3. The fixture of claim 1 wherein said rigid mass includes at least two separate rigid plates, each said plate having an inner surface with a portion of at least two separate said bores and a portion of at least two separate said voids formed therein, said bore portions and said void portions located on said inner surfaces at complementary locations on each said plate such that when said plates are located facing each other and adjacent each other, said at least two bores pass through said mass from said top to said bottom with one said void located within each said bore; and securing components provided on said fixture for securing said separate rigid plates together.

4. An apparatus for polishing and streamlining surfaces of a cylindrical radially expandable surgical stent, the apparatus comprising in combination:

a source of fluid abrasive media;

a fixture having a rigid mass with a top and a bottom, at least one bore in said mass passing from said top to said bottom, each said at least one bore configured to allow the abrasive media to flow through said bore, a void located within each said at least one bore and between a top and a bottom of said bore and having a width similar to an outer diameter of the stent and a length similar to a length of the stent;

each said bore having a width adjacent to upper and lower ends of a respective said void less than the outer diameter of the cylindrical radially expandable surgical stent, such that the stent cannot pass out of said void and into said respective bore, said bore having a substantially circular cross-section adjacent said void with a diameter similar to an inner diameter of the stent, such that the fluid abrasive media passing through said bore and into said void is shielded from hitting ends of the stent but rather flows adjacent to surfaces of the stent forming the inner diameter of the stent; and means to direct said fluid abrasive media from said source to each said at least one bore of said fixture and past the radially expandable surgical stent within a respective said void.

5. The polishing apparatus of claim 4 wherein each said void within said fixture is cylindrical in contour with a central axis and a diameter similar to an outer diameter of the cylindrical radially expandable surgical stent and wherein a respective said bore enters and exits said void in a direction parallel to a central axis of said bore.

6. The polishing apparatus of claim 5 wherein said apparatus further includes a means to reverse flow of said fluid abrasive media, such that said fluid abrasive media can flow either from said top of said mass to said bottom of said mass or from said bottom of said mass to said top of said mass, and wherein said apparatus includes means to vibrate said fluid abrasive media ultrasonically as said fluid abrasive media passes through each said void in said fixture and adjacent surfaces of the cylindrical radially expandable surgical stent.

7. A fixture for supporting cylindrical radially expandable surgical stents during a stent polishing procedure which uses contact of a fluid abrasive media with the surfaces of each stent in a honing process to polish the stents, the fixture comprising:

a rigid mass having a top and a bottom and defining a plurality of bores extending therethrough between said top and said bottom, each of said bores including a void therewithin;

said rigid mass including at least two separate rigid outer plates, each of said outer plates having an inner surface extending between said top and and said bottom of said rigid mass with a portion of at least two separate said bores and portions of at least two separate respective said voids formed therein, such that said bores coextend parallel to said inner surfaces of the at least two outer plates, said bore portions and said void portions located on said inner surfaces at complementary locations on each of said outer plates such that when said outer plates are located facing each other and adjacent each other, said at least two bores pass through said mass from said top to said bottom with one said void located within each said bore; and securing components provided on said fixture for securing said separate rigid plates together.

8. The fixture of claim 7 wherein said rigid mass includes at least one inner plate secured between said outer plates, said inner plate having opposed surfaces adjacent to surfaces of adjacent ones of said plates, with portions of at least two separate said bores and portions of at least two separate respective said voids formed therein, at locations complementary to said locations of said bore portions and said void portions located on said adjacent ones of said plates.

9. The fixture of claim 7 wherein each said void has a width similar to an outer diameter of the stent and a length similar to a length of the stent, and each said bore has a width adjacent to upper and lower ends of a respective said void less than the outer diameter of the cylindrical radially expandable surgical stent, such that the stent cannot pass out of said void and into said respective bore, said bore having a substantially circular cross-section adjacent said void with a diameter similar to an inner diameter of the stent, such that the fluid abrasive media passing through said bore and into said void is shielded from hitting ends of the stent but rather flows adjacent to surfaces of the stent forming the inner diameter of the stent.

10. An apparatus for polishing and streamlining surfaces of a plurality of cylindrical radially expandable surgical stents, the apparatus comprising in combination:

a source of fluid abrasive media;

a fixture having a rigid mass with a top and a bottom and defining a plurality of bores extending therethrough between said top and said bottom, each of said bores including a void therewithin;

said rigid mass including at least two separate rigid outer plates, each said plate having an inner surface extending between said top and said bottom of said rigid mass with portions of at least two separate said bores and portions of at least two separate respective said voids formed therein, such that said bores coextend parallel to said inner surfaces of the at least two outer plates, said bore portions and said void portions located on said inner surfaces at complementary locations on each of said outer plates such that when said plates are located facing each other and adjacent each other, said at least two bores pass through said mass from said top to said bottom with one said void located within each said bore;

securing components provided on said fixture for securing said separate rigid plates together; and a means to direct said fluid abrasive media from said source to said plurality of bores of said fixture and past the radially expandable surgical stents within respective ones of said voids.

11. The apparatus of claim 10 wherein said rigid mass includes at least one inner plate secured between said outer plates, said inner plate having opposed surfaces adjacent to surfaces of adjacent ones of said plates, with portions of at least two separate said bores and portions of at least two separate respective said voids formed therein, at locations complementary to said locations of said bore portions and said void portions located on said adjacent ones of said plates.

12. The apparatus of claim 10 wherein each said void has a width similar to an outer diameter of the stent and a length similar to a length of the stent, and each said bore has a width adjacent to upper and lower ends of a respective said void less than the outer diameter of the cylindrical radially expandable surgical stent, such that the stent cannot pass out of said void and into said respective bore, said bore having a substantially circular cross-section adjacent said void with a diameter similar to an inner diameter of the stent, such that the fluid abrasive media passing through said bore and into said void is shielded from hitting ends of the stent but rather flows adjacent to surfaces of the stent forming the inner diameter of the stent.

* * * * *